US00PP22648P2

(12) United States Plant Patent
Zaiger et al.

(10) Patent No.: US PP22,648 P2
(45) Date of Patent: Apr. 17, 2012

(54) INTERSPECIFIC TREE NAMED 'BETTY-COT'

(50) Latin Name: *Interspecific prunus*
Varietal Denomination: Betty-Cot

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 5 days.

(21) Appl. No.: 12/927,683

(22) Filed: Nov. 22, 2010

(51) Int. Cl.
*A01H 5/00* (2006.01)

(52) U.S. Cl. ..... Plt./180

(58) Field of Classification Search ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular bearer of large size fruit.
2. Relatively uniform ripening of fruit throughout tree.
3. Fruit with very good flavor and eating quality.
4. Fruit with an attractive orange flesh and skin color.
5. Fruit with good balance between acid and sugar.
6. Vigorous, semi-spreading tree growth.

1 Drawing Sheet

Botanical classification: Interspecific *prunus* species.

STATEMENT REGARDING FEDERALLY SPONSORED RESEARCH AND DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum, interspecifics and apricots, which are known to us, and mentioned herein, 'PA7005-8' Apricot (U.S. Plant Pat. No. 7,034), 'Royal Zee' Plum (U.S. Plant Pat. No. 5,486), 'Flavor Giant' Apricot (U.S. Plant Pat. No. 5,308) and the proprietary apricot selections '160LH550', '15W297', '60GA1060' and the proprietary plumcot selection '4G1180'.

ORIGIN OF THE VARIETY

The new and distinct variety of interspecific tree [(*Prunus armeniaca*×(*Prunus salicina*×*Prunus armeniaca*)×*Prunus salicina*)×*Prunus armeniaca*] was originated by us in our experimental orchard located near Modesto, Calif. as an open pollinated seedling from the proprietary seedling selection with field identification number '160LH550'. The seed parent (160LH550) originated by us from crosses between the following proprietary selections and varieties; apricot '15W297', plumcot '4G1180', 'Royal Zee' Plum (U.S. Plant Pat. No. 5,486), apricot '60GA1060', 'Flavor Giant' Apricot (U.S. Plant Pat. No. 5,308) and 'PA7005-8' Apricot (U.S. Plant Pat. No. 7,034). A large number of these open pollinated seedlings were budded to older trees of 'Nemaguard' Rootstock (non-patented) to accelerate rapid fruit production for evaluation. Under close observation, one such seedling exhibited desirable tree growth and fruit characteristics and was selected in 2001 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [(Apricot×(PlmCot)×Plum)×Apricot] is of large size, vigorous, semi-spreading growth and a productive and regular bearer of large, freestone, orange flesh fruit with very good flavor and eating quality. The fruit is further characterized by having an attractive orange skin color, firm flesh with good handling and shipping quality and being relatively uniform in size and maturity throughout the tree. In comparison to its immediate parent '160LH550', the new variety has higher colored orange flesh and skin color, and is approximately 13 days earlier in maturity.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, 5 years of age, its flowers, foliage and fruit, as based on observations of 5 year old specimens grown near Modesto, Calif., with color in accordance with Munsell Book of Color.

Tree:

*Size*.—Large, usually pruned to 3 to 3.5 meters in height and width for economical harvesting of fruit.

*Vigor*.—Vigorous, growth of 1.5 to 2 meters in height the first growing season. Varies with fertility and type of soil, climatic conditions and cultural practices.

*Form*.—Semi-spreading, usually pruned to vase shape.

*Branching habit*.—Semi-spreading, crotch angle approximately 35°, increases with heavy crop load.

*Productivity*.—Productive, thinning and spacing of fruit desirable. Fruit set varies with climatic conditions during blooming period.

*Bearer*.—Regular, has set an adequate crop 3 consecutive years. No alternate bearing observed.

*Fertility*.—Self-fertile.

*Density*.—Medium dense, usually pruned to vase shape to allow more sunlight to center of tree to enhance fruit color and health of fruit spurs.

*Hardiness*.—Tree grown in USDA Hardiness Zone 9. Winter chilling requirement approximately 750 hours at or below 45° F. Hardy in all stone fruit growing areas of California.

Trunk:

*Size*.—Medium. Average circumference 58.4 cm at 25.4 cm above ground on a 5 year old tree.

*Stocky*.—Medium stocky.

*Texture*.—Medium shaggy, increases with age of growth.

*Color*.—Varies from 7.5YR 3/4 to 7.5 to 7.5 4/1.

Branches:

*Size*.—Medium. Average circumference 15.2 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 30 in a 25.8 sq cm surface area of branch. Average length 2.1 mm. Average width 1.5 mm. Color varies from 10YR 7/8 to 10YR 6/8.

*Color*.—New growth 2.5GY 5/8 with 7.5R 3/6. Old growth 5YR 3/4 to 7.5YR 4/2, varies with age of growth.

Leaves:

*Size*.—Medium. Average length 66.2 mm. Average width 61.1 mm.

*Form*.—Ovate.

*Apex*.—Cuspidate.

*Base*.—Obtuse.

*Margin*.—Serrulate.

*Thickness*.—Medium.

*Surface Texture*.—Upper surface relatively smooth, very slightly indented over midrib and leaf veins, glabrous. Lower surface relatively smooth, except for small ridges caused by midrib and pinnate venation, glabrous.

*Petiole*.—Average length 27.9 mm. Average width 1.5 mm. Longitudinally grooved. Surface glabrous. Color varies from 5R 3/2 to 7.5R 2/4.

*Glands*.—Type — globose. Size — small to medium. Average length 0.9 mm. Average width 0.7 mm. Number — average 3, varies from 1 to 4. Located primarily on upper portion of petiole, base of leaf blade. Color varies from 5R 3/6 to 5R 3/8.

*Stipules*.—No stipules present.

*Color*.—Upper surface varies from 5GY 3/4 to 7.5GY 2/4. Lower surface varies from 7.5GY 4/4 to 10GY 4/4. Midvein color varies from 2.5GY 7/4 to 7.5R 4/6.

Flower buds:

*Size*.—Medium to large. Average length 15.4 mm. Average diameter 9.5 mm.

*Hardiness*.—Hardy with respect to California winters.

*Form*.—Conical, becoming slightly elongated just before opening.

*Pedicel*.—Short. Average length 1.9 mm. Average width 1.3 mm. Color varies from 2.5GY 7/6 to 2.5GY 6/6.

*Color*.—Varies from 7.5RP 7/8 to 7.5RP 8/4.

*Number of buds per spur*.—Varies from 10 to 18, varies with age of spur.

Flowers:

*Blooming period*.—Date of First Bloom Feb. 14, 2010. Date of Petal Fall Feb. 24, 2010, varies slightly with climatic conditions.

*Size*.—Medium to large. Average height 18.2 mm. Average diameter 28.3 mm.

*Petals*.—Number — 5, alternately arranged to sepals. Size — medium. Average length 13.9 mm. Average width 15.3 mm. Shape — ovate. Margin — entire. Both upper and lower surfaces glabrous. Color — upper surface varies from 5R 3/6 to 2.5R 3/6. Lower surface varies from 2.5R 5/8 to 5R 2/6.

*Sepals*.—Number — 5, alternately arranged to petals. Size — small to medium. Average length 5.2 mm. Average width 5.3 mm. Shape — ovate. Margin — entire. Both upper and lower surfaces glabrous. Color — upper surface varies from 5R 3/6 to 2.5R 3/6. Lower surface varies from 2.5R 3/8 to 5R 2/6.

*Stamens*.—Average number per flower 31. Average filament length 12.8 mm. Filament color N 9.5/(white). Anther color varies from 5Y 8/10 to 5Y 7/10.

*Pollen*.—Self fertile, fruit set while under a bag. Color varies from 2.5Y 7/12 to 5Y 7/10.

*Pistil*.—Normally 1. Surface — pubescent. Average length 14.6 mm. Position of stigma average of 1.3 mm below anthers. Color varies from 10Y 8/4 to 10Y 7/6.

*Fragrance*.—Heavy.

*Color*.—Varies from 5RP 9/2 to 7.5RP 9/2.

*Number flowers per flower bud*.—Usually 1, varies from 1 to 4.

*Pedicel*.—Average length 2.6 mm. Average width 1.7 mm. Color varies from 10Y 7/6 to 2.5GY 8/6.

Fruit:

*Maturity when described*.—Firm ripe.

*Date of first picking*.—May 27, 2010.

*Date of last picking*.—Jun. 3, 2010, varies slightly with climatic conditions.

*Size*.—Medium to large. Average diameter axially 59.1 mm. Average transversely in suture plane 58.7 mm. Average across suture plane 55.6 mm. Average weight 107.9 grams, average weight varies slightly with fertility of the soil, amount of thinning and climatic conditions.

*Form*.—Slightly elongated, slightly flatted inward toward suture plane.

*Suture*.—Distinct, extends from base to apex.

*Ventral surface*.—Lipped, well sealed.

*Apex*.—Slightly retuse.

*Base*.—Flat to slightly retuse.

*Stem cavity*.—Rounded to slightly elongated in suture plane. Average depth 4.3 mm. Average diameter 5.7 mm.

Stem:

*Size*.—Small. Average length 7.3 mm. Average diameter 3.7 mm.

*Color*.—Varies from 2.5GY 7/8 to 5GY 6/8.

Flesh:

*Ripens*.—Evenly.

*Texture*.—Firm, meaty.

*Fibers*.—Few, small, tender.

*Firmness*.—Firm, firmer than most commercial apricots.

*Aroma*.—Moderate.

*Amydgalin*.—Slight.

*Eating quality*.—Very good.

*Flavor*.—Very good, good balance between acid and sugar.

*Juice*.—Moderate, enhances flavor.

*Brix*.—Average 16.0°, varies slightly with amount of fruit per tree and climatic conditions.

*Color*.—Varies from 2.5YR 5/10 to 5YR 6/10. Pit cavity 2.5YR 5/10.

Skin:

*Thickness*.—Medium.

*Surface*.—Nearly smooth, very slightly waffled.

*Pubescence*.—Light amount, very short in length.

*Tendency to crack*.—None.

*Color*.—Ground color varies from 2.5YR 6/10 to 2.5YR 5/10. Overspread with 5R 4/10 where exposed to sun.

*Tenacity*.—Tenacious to flesh.

*Astringency*.—Slight to none.

Stone:

*Type*.—Freestone.

*Size*.—Large. Average length 30.2 mm. Average width 22.9 mm. Average depth 14.2 mm.

*Form*.—Ovoid.

*Base*.—Usually flat, varies on some stones from flat to slightly rounded.

*Apex*.—Slightly pointed. Average length 1.8 mm.

*Surface*.—Slightly pitted throughout. Pits vary from round to elongated.

*Sides*.—Unequal, one side extending further from suture plane.

*Ridges*.—Small, narrow ridge next to suture, extending from base to apex.

*Tendency to split*.—None.

*Color*.—Varies from 10YR 7/4 to 7.5YR 4/2 when dry.

*Pit cavity*.—Average length 32.0 mm. Average depth 8.4 mm.

Kernel:

*Size*.—Large. Average length 19.7 mm. Average width 13.2 mm. Average depth 8.0 mm.

*Form*.—Ovate.

*Viability*.—Viable, complete embryo development.

*Skin color*.—Varies from 5Y 9/4 to 7.5Y 9/4.

Use: Dessert.

*Market*.—Local and long distance.

Keeping quality: Good, held firm in cold storage 2 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct interspecific tree substantially as illustrated and described.

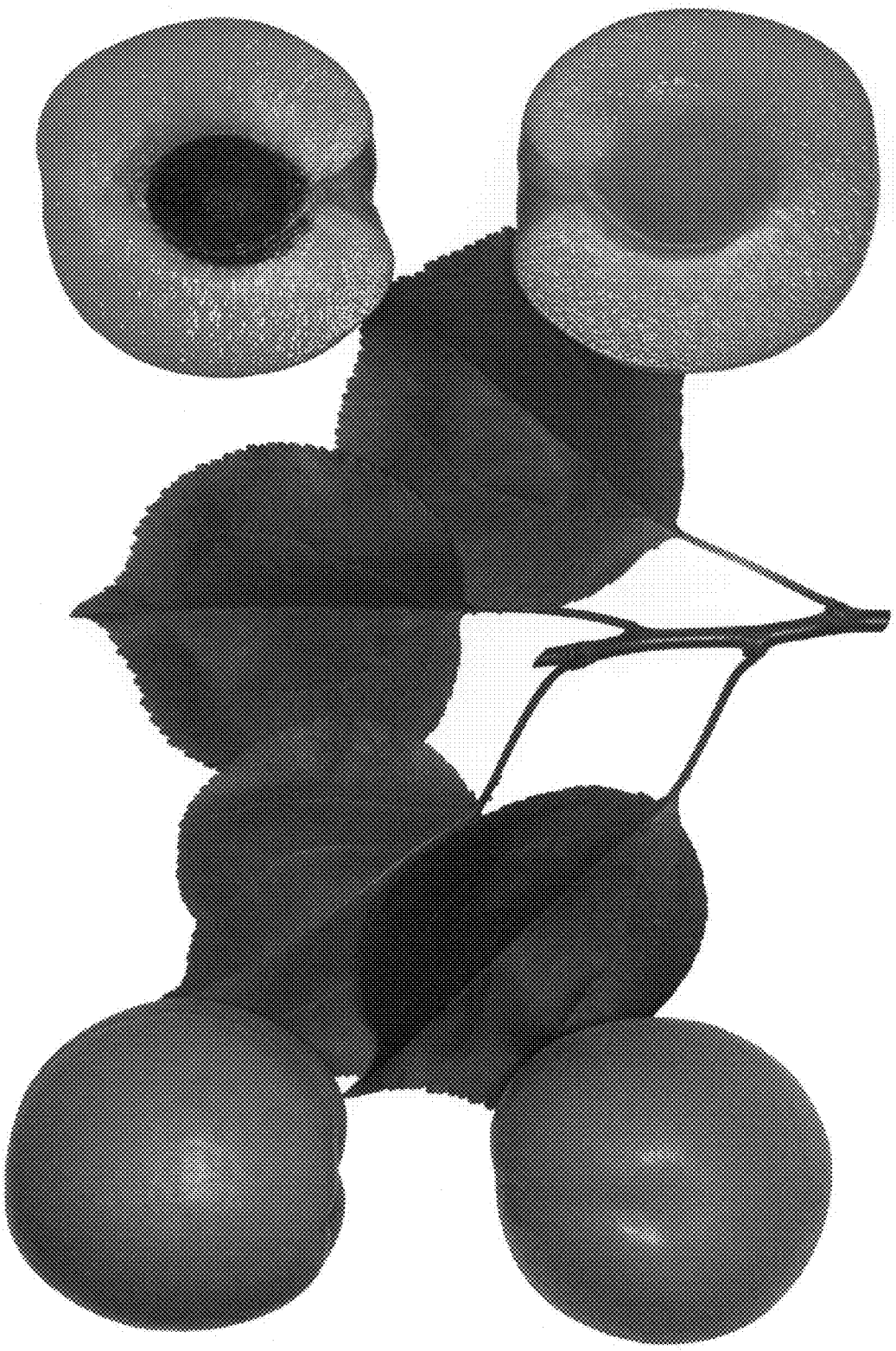

* * * * *